US008916613B2

(12) United States Patent
Andersch et al.

(10) Patent No.: US 8,916,613 B2
(45) Date of Patent: Dec. 23, 2014

(54) SYNERGISTIC INSECTICIDAL MIXTURES

(75) Inventors: Wolfram Andersch, Bergisch Gladbach (DE); Heike Hungenberg, Langenfeld (DE); Wolfgang Thielert, Odenthal (DE)

(73) Assignee: Bayer CropScience AG, Monheim (DE)

( * ) Notice: Subject to any disclaimer, the term of this patent is extended or adjusted under 35 U.S.C. 154(b) by 166 days.

(21) Appl. No.: 12/761,128

(22) Filed: Apr. 15, 2010

(65) Prior Publication Data
US 2010/0197747 A1 Aug. 5, 2010

Related U.S. Application Data

(63) Continuation of application No. 10/582,134, filed as application No. PCT/EP2004/013470 on Nov. 27, 2004, now abandoned.

(30) Foreign Application Priority Data

Dec. 12, 2003 (DE) .................................. 103 58 181
Jun. 16, 2004 (DE) ......................... 10 2004 028 995

(51) Int. Cl.
| | |
|---|---|
| A01N 37/52 | (2006.01) |
| A61K 31/155 | (2006.01) |
| A01N 33/00 | (2006.01) |
| A61K 31/13 | (2006.01) |
| A61K 31/16 | (2006.01) |
| A01N 37/18 | (2006.01) |
| A01N 25/00 | (2006.01) |
| A61K 47/00 | (2006.01) |
| A01N 47/24 | (2006.01) |
| A01N 43/40 | (2006.01) |
| A01N 43/50 | (2006.01) |
| A01N 43/88 | (2006.01) |
| A01N 47/40 | (2006.01) |
| A01N 47/44 | (2006.01) |

(52) U.S. Cl.
CPC .............. *A01N 47/24* (2013.01); *A01N 43/40* (2013.01); *A01N 43/50* (2013.01); *A01N 43/88* (2013.01); *A01N 47/40* (2013.01); *A01N 47/44* (2013.01)
USPC ........... 514/634; 514/579; 514/613; 514/631; 514/788

(58) Field of Classification Search
USPC ........................ 514/634, 579, 613, 631, 788
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 4,849,432 A | 7/1989 | Shiokawa et al. | |
| 5,876,739 A | 3/1999 | Turnblad et al. | |
| 6,306,414 B1 | 10/2001 | Koike | |
| 6,436,976 B1 | 8/2002 | Erdelen et al. | |
| 6,479,542 B2 | 11/2002 | Sembo et al. | |
| 6,534,529 B2 | 3/2003 | Uhr et al. | |
| 6,680,325 B2 | 1/2004 | Erdelen et al. | |
| 6,828,275 B2 | 12/2004 | Uhr et al. | |
| 7,232,840 B2 | 6/2007 | Erdelen et al. | |
| 7,659,228 B2 | 2/2010 | Uhr et al. | |
| 2001/0014347 A1* | 8/2001 | Koike ........................... 424/409 |
| 2003/0153464 A1* | 8/2003 | Nakamura et al. ............ 504/257 |
| 2003/0176428 A1 | 9/2003 | Schneidersmann et al. | |
| 2003/0232821 A1 | 12/2003 | Maienfisch et al. | |
| 2005/0009883 A1 | 1/2005 | Uhr et al. | |
| 2005/0197251 A1 | 9/2005 | Ding et al. | |
| 2006/0004070 A1 | 1/2006 | Wachendorff-Neumann et al. | |
| 2006/0035942 A1 | 2/2006 | Wachendorff-Neumann et al. | |
| 2006/0276342 A1 | 12/2006 | Krahmer et al. | |
| 2007/0037799 A1 | 2/2007 | Dahmen et al. | |
| 2007/0054804 A1 | 3/2007 | Suty-Heinze | |
| 2007/0078171 A1 | 4/2007 | Andersch et al. | |
| 2007/0142327 A1 | 6/2007 | Funke et al. | |
| 2007/0155797 A1 | 7/2007 | Andersch et al. | |
| 2007/0203025 A1 | 8/2007 | Bickers et al. | |
| 2007/0203208 A1 | 8/2007 | Erdelen et al. | |
| 2007/0213396 A1 | 9/2007 | Thielert et al. | |
| 2007/0232598 A1 | 10/2007 | Funke et al. | |
| 2007/0270416 A1 | 11/2007 | Funke et al. | |
| 2007/0287720 A1 | 12/2007 | Royalty et al. | |
| 2008/0027114 A1 | 1/2008 | Funke et al. | |
| 2008/0070863 A1 | 3/2008 | Funke et al. | |
| 2008/0261811 A1 | 10/2008 | Krohn et al. | |

(Continued)

FOREIGN PATENT DOCUMENTS

| | | |
|---|---|---|
| EP | 0 235 725 A2 | 9/1987 |
| EP | 0 376 279 A2 | 7/1990 |
| EP | 0 580 553 A2 | 1/1994 |
| EP | 0 649 845 A1 | 4/1995 |
| EP | 1 198 170 B1 | 12/2005 |
| JP | 07-126113 | 5/1995 |
| WO | WO 97/40692 A1 | 11/1997 |
| WO | WO 00/54591 A2 | 9/2000 |
| WO | WO 02/17720 A1 | 3/2002 |
| WO | WO 02/28186 A2 | 4/2002 |

(Continued)

OTHER PUBLICATIONS

Bauer, T.A., et al., "Response of Selected Weed Species to Postemergence Imazethapyr and Bentazon," *Weed Tech.* 9:236-242, The Weed Science Society of America (1995).

(Continued)

*Primary Examiner* — Mina Haghighatian
*Assistant Examiner* — Helen Chui
(74) *Attorney, Agent, or Firm* — Sterne, Kessler, Goldstein & Fox P.L.L.C

(57) ABSTRACT

The invention relates to insecticide mixtures comprising thiodicarb and at least one other known active ingredient from the category of chloronicotinyls, as well as the use of these mixtures to control animal pests.

4 Claims, No Drawings

(56) References Cited

U.S. PATENT DOCUMENTS

| | | |
|---|---|---|
| 2008/0269051 A1 | 10/2008 | Suty-Heinze et al. |
| 2008/0269263 A1 | 10/2008 | Dahmen et al. |
| 2008/0274882 A1 | 11/2008 | Krohn et al. |
| 2009/0156399 A1 | 6/2009 | Hungenberg et al. |
| 2009/0170912 A1 | 7/2009 | Erdelen et al. |
| 2009/0215760 A1 | 8/2009 | Hungenberg et al. |
| 2009/0286681 A1 | 11/2009 | Dahmen et al. |
| 2010/0041659 A1 | 2/2010 | Dutzmann et al. |
| 2010/0113268 A1 | 5/2010 | Andersch et al. |
| 2010/0210691 A1 | 8/2010 | Dutzmann et al. |

FOREIGN PATENT DOCUMENTS

| | | |
|---|---|---|
| WO | WO 02/48137 A2 | 6/2002 |
| WO | WO 02/49430 A1 | 6/2002 |
| WO | WO 02/080675 A1 | 10/2002 |
| WO | WO 03/061383 A1 | 7/2003 |

OTHER PUBLICATIONS

Blackshaw, R.E., et al., "Herbicide Combinations for Postemergent Weed Control in Safflower (*Carthamus tinctorius*)," *Weed Tech.* 4:97-104, The Weed Science Society of America (1990).

Blackshaw, R.E., "HOE-39866 Use in Chemical Fallow Systems," *Weed Tech.* 3:420-428, The Weed Science Society of America (1989).

Blackshaw, R.E., "Synergistic Mixes of DPX-A7881 and Clopyralid in Canola (*Brassica napus*)," *Weed Tech.* 3:690-695, The Weed Science Society of America (1989).

Blouin, D.C., et al., "Analysis of Synergistic and Antagonistic Effects of Herbicides Using Nonlinear Mixed-Model Methodology," *Weed Tech.* 18:464-472, The Weed Science Society of America (2004).

Bradley, P.R., et al., "Response of Sorghum (*Sorghum bicolor*) to Atrazine, Ammonium Sulfate, and Glyphosate," *Weed Tech.* 14:15-18, The Weed Science Society of America (2000).

Buker, III, R.S., et al., "Confirmation and Control of a Paraquat-Tolerant Goosegrass (*Eleusine indica*) Biotype," *Weed Tech.* 16:309-313, The Weed Science Society of America (2002).

Burke, I.C., et al., "CGA-362622 Antagonizes Annual Grass Control with Clethodim," *Weed Tech.* 16:749-754, The Weed Science Society of America (2002).

Flint, J.L., et al., "Analyzing Herbicide Interactions, A Statistical Treatment of Colby's Method," *Weed Tech.* 2:304-309, The Weed Science Society of America (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America (1988).

Harker, N.K., and O'Sullivan, P.A., "Synergistic Mixtures of Sethoxydim and Fluazifop on Annual Grass Weeds," *Weed Tech.* 5:310-316, The Weed Science Society of America (1991).

Kent, L.M., et al., "Effect of Ammonium Sulfate, Imazapyr, and Environment on the Phytotoxicity of Imazethapyr," *Weed Tech.* 5:202-205, The Weed Science Society of America (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America (1996).

Lanclos, D.Y., et al., "Glufosinate Tank-Mix Combinations in Glufosinate-Resistant Rice (*Otyza sativa*)," *Weed Tech.* 16:659-663, The Weed Science Society of America (2002).

Norris, J.L., et al., "Weed Control from Herbicide Combinations with Three Formulations of Glyphosate," *Weed Tech.* 15:552-558, The Weed Science Society of America (2001).

Novosel, K.M., et al., "Metolachlor Efficacy as Influenced by Three Acetolactate Synthase-Inhibiting Herbicides," *Weed Tech.* 12:248-253, The Weed Science Society of America (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America (2000).

Salzman, F.P., and Renner, K.A., "Response of Soybean Combinations of Clomazone, Metribuzin, Linuron, Alachlor, and Atrazine," *Weed Tech.* 6:922-929, The Weed Science Society of America (1992).

Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech.* 12:463-469, The Weed Science Society of America (1998).

Shaw, D.R. and Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination with Pyrithiobac," *Weed Tech.* 10:889-892, The Weed Science Society of America (1996).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America (1997).

Zhang, W., et al., "Fenoxaprop Interactions for Barnyardgrass (*Echinochloa crus-galli*) Control in Rice," *Weed Tech.* 19:293-297, The Weed Science Society of America (2005).

Office Action mailed Sep. 8, 2003, in U.S. Appl. No. 10/348,251, Uhr et al., filed Jan. 21, 2003, issued on Dec. 7, 2004, as U.S. Patent No. 6,828,275.

Co-pending U.S. Appl. No. 12/671,544, filed Feb. 1, 2010, inventors Hungenberg et al. (Not Published).

Co-pending U.S. Appl. No. 10/581,348, inventors Funke, C., et al., filed Nov. 20, 2004 (Not Published).

Co-pending U.S. Appl. No. 11/629,873, inventors Hungenberg, H., et al., filed Jun. 9, 2005.

Co-pending U.S. Appl. No. 11/997,079, inventors Dr. Dhamen, P., et al., filed Jul. 15, 2006.

Co-pending U.S. Appl. No. 12/063,793, inventors Hungenberg, H., et al., filed Aug. 3, 2006.

Co-pending U.S. Appl. No. 11/910,659, inventors Wachendorff-Neumann U., et al., filed Mar. 27, 2007 (Not Published).

Millstone, E., "Food additives: the balance of risks and benefits," *Chem. Ind.*:730-733, Society of Chemical Industry, England (1985).

Notice of Allowance mailed Aug. 24, 2010, in U.S. Appl. No. 12/776,345, Dutzmann et al., filed May 7, 2010.

Rummens, F.H.A., "An Improved Definition of Synergistic and Antagonistic Effects," *Weed Science* 23:4-6 (1975).

Unverified English language translation of JP 07-126113 A.

Unverified English language translation of a third party's submission in Brazilian Patent Application No. PI0406186-1, the Brazilian national phase entry of PCT/EP2004/013470.

"Thiodicarb," *Pest. Manual*, 13$^{th}$ edition, CDS Tomlin ed., pp. 969-970, British Crop Protection Council (2003).

Office Action mailed Jan. 27, 2009 in U.S. Appl. No. 10/582,134, Andersch et al., filed Jun. 8, 2006.

Office Action mailed Nov. 24, 2009, in U.S. Appl. No. 10/582,134, Andersch et al., filed Jun. 8, 2006.

Office Action mailed Apr. 10, 2013 in U.S. Appl. No. 10/582,134, Andersch et al., filed Jun. 8, 2006.

"Acephate," in *The Pesticide Manual: A World Compendium*, 13$^{th}$ edition, Tomlin, C.D.S., ed., British Crop Protection Council, Hampshire, UK, entry 4 (Nov. 2003).

"Acetamiprid," in *The Pesticide Manual: A World Compendium*, 11$^{th}$ edition, Tomlin, C.D.S., ed., British Crop Protection, Hampshire, UK, entry 5 (1997).

"Clothianidin," in *The Pesticide Manual: A World Compendium*, 13$^{th}$ edition, Tomlin, C.D.S., ed., British Crop Protection Council, Hampshire, UK, entry 165 (Nov. 2003).

Colby, S.R., "Calculating Synergistic and Antagonistic Responses of Herbicide Combinations," *Weeds* 15:20-22, Weed Society of America (1967).

"Disodium S,S'-(2-dimethylamino=trimethylene)di(thiosulfate)," in *The Pesticide Manual: A World Compendiume*, 13$^{th}$ edition, Tomlin, C.D.S., ed., British Crop Protection Council, Hampshire, UK, entry 271 (Nov. 2003).

(56) References Cited

OTHER PUBLICATIONS

"Imidacloprid," in *The Pesticide Manual: A World Compendium, 11th edition*, Tomlin, C.D.S., ed., British Crop Protection, Hampshire, UK, entry 418(1997).

"Iprodione," in *The Pesticide Manual: A World Compendium, 13th edition*, Tomlin, C.D.S., ed., British Crop Protection Council, Hampshire, UK, entry 458 (Nov. 2003).

"Nitenpyram," in *The Pesticide Manual: A World Compendium, 11th edition*, Tomlin, C.D.S., ed., British Crop Protection, Hampshire, UK, entry 521 (1997).

"Oxadiazon," in *The Pesticide Manual: A World Compendium, 13th edition*, Tomlin, C.D.S., ed., British Crop Protection Council, Hampshire, UK, entry 579 (Nov. 2003).

"Thiodicarb," in *The Pesticide Manual: A World Compendium, 11th edition*, Tomlin, C.D.S., ed., British Crop Protection, Hampshire, UK, entry 708 (1997).

"Trifluralin," in *The Pesticide Manual: A World Compendium, 13th edition*, Tomlin, C.D.S., ed., British Crop Protection Council, Hampshire, UK, entry 791 (Nov. 2003).

"Triflusolfuron-methyl," in *The Pesticide Manual: A World Compendium, 13th edition*, Tomlin, C.D.S., ed., British Crop Protection Council, Hampshire, UK, entry 792 (Nov. 2003).

"Uniconazole," in *The Pesticide Manual: A World Compendium, 13th edition*, Tomlin, C.D.S., ed., British Crop Protection Council, Hampshire, UK, entry 799 (Nov. 2003).

Esp@cenet database, English language abstract for JP-H7-126113, published on May 16, 1995.

International Search Report of International Application PCT/EP2004/013470, European Patent Office, Netherlands, mailed on Apr. 20, 2005.

Office Action mailed Jun. 19, 2012, in U.S. Appl. No. 10/582,134, Andersch et al., filed Jun. 8, 2006.

\* cited by examiner

SYNERGISTIC INSECTICIDAL MIXTURES

The present invention relates to new combinations of active ingredients that comprise the active ingredients thiodicarb and an additional active ingredient from the category of chloronicotinyls and that possess very good insecticidal properties.

It is already known that thiodicarb can be used to control animal pests, especially insects. Furthermore, it is known that chloronicotinyls such as imidacloprid, thiacloprid, clothianidin, thiamethoxam, acetamiprid, nitenpyram and dinotefuran are suitable for controlling animal pests, especially insects.

The efficacy of these compounds is good, but falls short in some cases when small quantities are applied or when used on individual pests.

It has now been found that mixtures comprising thiodicarb and one compound from the category of chloronicotinyls are synergistically effective and are suitable for controlling animal pests. This synergy makes it possible to use markedly smaller quantities of the active ingredient, i.e. the effect of the mixture is greater than the effect of the individual components.

The mentioned compounds are known, for example, from *The Pesticide Manual*, 11th edition, 1997, published by the British Crop Protection Council, see page 1195 for thiodicarb, page 706 for imidacloprid, page 9 for acetamiprid and page 880 for nitenpyram.

The formula for thiamethoxam is

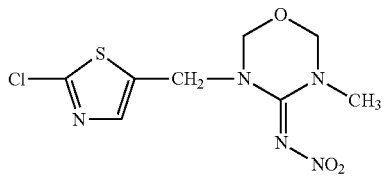 [SMILES: CN1COCN(Cc2cnc(Cl)s2)/C1=N/[N+](=O)[O-]]

and is known from EP 0 580 553.

The formula for clothianidin is

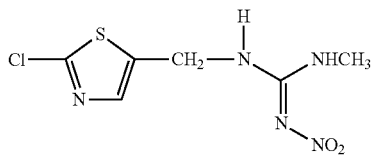 [SMILES: CN/C(=N\[N+](=O)[O-])NCc1cnc(Cl)s1]

and is known from EP 0 376 279.

The formula for thiacloprid is

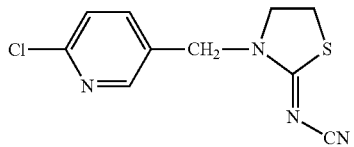 [SMILES: N#C/N=C1\SCCN1Cc1ccc(Cl)nc1]

and is known from EP 0 235 725.

The formula for dinotefuran is

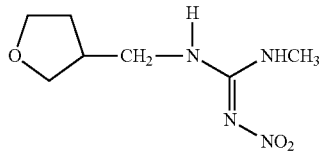

and is known from EP 0 649 845.

The proportion of the utilised active ingredients to one another, as well as the total amount of the mixture to be applied depends on the species and occurrence of the insects. The optimal proportions and total amounts used can be determined by test series for each application.

A particularly preferred mixture according to the invention comprises the active ingredients thiodicarb and imidacloprid. In the mixture the weight ratio of the two substances in relation to each other is preferred between 100 to 1 and 1 to 50 and particularly preferred between 25 to 1 and 1 to 5, whereby here, as below, thiodicarb is referred to first in each case in the ratios.

Another particularly preferred mixture according to the invention comprises the active ingredients thiodicarb and acetamiprid. In the mixture the weight ratio of the two active ingredients is preferred between 100 to 1 and 1 to 50 and particularly preferred between 25 to 1 and 1 to 5.

Another particularly preferred mixture according to the invention comprises the active ingredients thiodicarb and nitenpyram. In the mixture the weight ratio of the two active ingredients is preferred between 100 to 1 and 1 to 50 and particularly preferred between 25 to 1 and 1 to 5.

Another particularly preferred mixture according to the invention comprises the active ingredients thiodicarb and dinotefuran. In the mixture the weight ratio of the two active ingredients is preferred between 100 to 1 and 1 to 50 and particularly preferred between 25 to 1 and 1 to 5.

Another particularly preferred mixture according to the invention comprises the active ingredients thiodicarb and thiamethoxam. In the mixture the weight ratio of the two active ingredients is preferred between 100 to 1 and 1 to 50 and particularly preferred between 25 to 1 and 1 to 5.

Another particularly preferred mixture according to the invention comprises the active ingredients thiodicarb and clothianidin. In the mixture the weight ratio of the two active ingredients is preferred between 100 to 1 and 1 to 50 and particularly preferred between 25 to 1 and 1 to 5.

Another particularly preferred mixture according to the invention comprises the active ingredients thiodicarb and thiacloprid. In the mixture the weight ratio of the two active ingredients is preferred between 100 to 1 and 1 to 50 and particularly preferred between 25 to 1 and 1 to 5.

The active ingredient combinations, having good plant tolerability and favourable toxicity to warm-blooded animals, are suitable for controlling animal pests, especially insects, arachnids and nematodes, that occur in agriculture, forestry, stored product protection and materials protection, as well as in the sanitation sector. They can be used preferably as pesticides. They are effective for normally sensitive and resistant species, as well as for all life stages, or individual stages. The above-mentioned pests include:

From the order Isopoda, e.g., *Oniscus asellus, Armadillidium vulgare, Porcellio scaber.*

From the order Diplopoda, e.g., *Blaniulus guttulatus.*

From the order Chilopoda, e.g., *Geophilus carpophagus, Scutigera* spp.

From the order Symphyla, e.g., *Scutigerella immaculata.*

From the order Thysanura, e.g., *Lepisma saccharina.*

From the order Collembola, e.g., *Onychiurus armatus.*

From the order Orthoptera, e.g., *Acheta domesticus, Gryllotalpa* spp., *Locusta migratoria migratorioides, Melanoplus* spp., *Schistocerca gregaria.*

From the order Blattaria, e.g., *Blatta orientalis, Periplaneta americana, Leucophaea maderae, Blattella germanica.*

From the order Deimaptera, e.g., *Forficula auricularia.*

From the order Isoptera, e.g., *Reticulitermes* spp.

From the order Phthiraptera, e.g., *Pediculus humanus corporis, Haematopinus* spp., *Linognathus* spp., *Trichodectes* spp., *Damalinia* spp.

From the order Thysanoptera, e.g., *Hercinothrips femoralis, Thrips tabaci, Thrips palmi, Frankliniella occidentalis.*

From the order Heteroptera, e.g., *Eurygaster* spp., *Dysdercus intermedius, Piesma quadrata, Cimex lectularius, Rhodnius prolixus, Triatoma* spp.

From the order Homoptera, e.g., *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order Lepidoptera e.g, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order Coleoptera, e.g., *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order Hymenoptera, e.g., *Diprion* spp., *Hoplocampa* spp., *Lasius* spp., *Monomorium pharaonis, Vespa* spp.

From the order Diptera, e.g., *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order Siphonaptera, e.g., *Xenopsylla cheopis, Ceratophyllus* spp.

From the class Arachnida, e.g., *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, e.g., *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

In accordance with the invention all plants and plant parts can be treated. Plants are understood here to be all plants and plant populations, such as desirable and undesirable wild plants or cultivated plants (including naturally occurring cultivated plants). Cultivated plants can be plants that can be acquired through conventional breeding and optimization methods or through biotechnological methods and genetic engineering or combinations of these methods, including transgenic plants and including plant species than can and cannot be protected by plant breeder's rights. Plant parts are understood to be all above-ground and underground plant parts and organs, such as the shoot, leaf, flower and root, whereby leaves, needles, stalks, stems, flowers, receptacles, fruits and seeds, as well as roots, tubers and rhizomes are listed as examples. Plant parts also include harvested crops, as well as vegetative and generative propagation material, for example shoots, tubers, rhizomes, runners and seeds.

Hereby the particularly advantageous effect of the compounds of the invention is emphasized in regard to application to cereals, such as wheat, oats, barley, spelt, triticale and rye, as well as corn, millet, rice, sugarcane, soy, sunflowers, potatoes, cotton, rapeseed, canola, tobacco, sugar beets, fodder beets, asparagus, hops, and fruit plants (including pomeaceous fruits such as apples and pears; stone fruits such as peaches, nectarines, cherries, plums and apricots; citrus fruits such as oranges, grapefruits, limes, lemons, kumquats, mandarins and satsumas; nuts such as pistachios, almonds, walnuts and pecans; tropical fruits such as mango, papaya, pineapple, dates and bananas; and grapes) and vegetables [including leafy green vegetables such as endives, corn salad, Florence fennel, head and loose-leaf lettuce, common beets, spinach and Belgian endive; cole crops such as cauliflower, broccoli, Chinese cabbage, kale (green or curly kale), kohlrabi, Brussels sprouts, red cabbage, white cabbage and savoy cabbage; fruiting vegetables such as eggplants, cucumbers, peppers, edible pumpkins and squashes, tomatoes, zucchini and sweet corn; root vegetables such as celeriac, turnips, carrots, baby carrots, radishes, baby radishes, garden beets, black salsify, celery; legumes such as peas and beans; and alliums such as leeks and onions].

The treatment of plants and plant parts with the active ingredient combinations in accordance with the invention occurs directly, or through action on the environment, habitat or storage area in accordance with customary treatment methods, e.g., dipping, spraying, vaporizing, nebulising, sprinkling, coating, and for propagation material, in particular seeds, by one-layer or multi-layer encasing of the seeds.

The mixtures in accordance with the invention are particularly suited for treating seed. A large part of the damage to cultivated plants by pests occurs when the seeds are infested during storage and after the seeds have been sown in the soil, as well as during and immediately after plant germination. This phase is especially critical since the roots and shoots of the growing plant are particularly sensitive, and even minor damage can result in the death of entire plant. Therefore, there is a great deal of interest in protecting seeds and germinating plants through the use of appropriate means.

It has been known for years that treating plant seeds can control pests, and treatments are continually being improved. When treating seeds, however, there is a series of problems that can arise, which cannot always be solved satisfactorily. Therefore it is worthwhile to develop processes that protect seeds and germinating plants and that make unnecessary the deployment of pesticides after sowing or after plants have emerged. It is furthermore worthwhile to optimize the amount of active ingredient used so that the seeds and the germinating plants are protected as much as possible before being infested by pests without damaging the plant itself with the active ingredient used. In particular, processes for treating seeds should also take into account the intrinsic insecticidal properties of transgenic plants in order to optimally protect seeds and germinating plants while using the minimum amount of pesticides.

Therefore the present invention relates in particular to a process for protecting seeds and germinating plants before they have been infested by pests by treating the seeds with a composition in accordance with the invention. The invention also relates to the use of the compositions of the invention for treating seeds to protect them and germinating plants from pests. Furthermore, the invention relates to seeds that have been treated with a composition of the invention to protect them from pests.

One of the advantages of the present invention is that, due to the special systemic properties of the compositions of the invention, the treatment of seeds with these compositions protects from pests both the seeds themselves and the plants that emerge from them after germination. This makes it unnecessary to immediately treat the culture during sowing or shortly thereafter.

Another advantage relates to the synergistic increase of the insecticidal efficacy of the composition of the invention compared to the respective single active ingredient, wherein the increase of efficacy is greater than the sum of the efficacy of the two separately applied active ingredients. This allows the optimization of the quantity of active ingredient to be used.

It is also considered advantageous that the mixtures according to the invention in particular can also be used for transgenic seed, whereby the plants that emerge from this seed can express a protein that is targeted against pests. By treating such seed with the compositions of the invention certain pests can be controlled just through the expression of, e.g., an insecticidal protein, resulting surprisingly in synergistically increased efficacy with the compositions of the invention, which further improves the effectiveness of the protection against infestation.

The compositions of the invention are suitable for protecting seeds of all plant species as already listed above, which are used in agriculture, forestry, horticulture and viniculture. In particular this refers to the seed of corn, peanuts, canola, rape, poppy, olive, coconut, cocoa, soy, cotton, beets (sugar and fodder beets), rice, millet, wheat, barley, oats, rye, sunflower, sugarcane and tobacco. The compositions of the invention are also suitable for treating the seed of fruiting plants and vegetables such as those already listed above. Of particular importance is the treatment of the seed of corn, soy, cotton, wheat and canola or rape.

As already mentioned previously, the treatment of transgenic seed with a composition of the invention is of particular importance. What is being referred to is the seed of plants that as a rule possess at least one heterologous gene that controls the expression of a polypeptide with particular insecticidal properties. The heterologous genes in transgenic seed can originate from microorganisms such as *Bacillus, Rhizobium, Pseudomonas, Serratia, Trichoderma, Clavibacter, Glomus* and *Gliocladium*. The present invention is particularly suited for treating transgenic seed that possesses at least one heterologous gene that originated from *Bacillus* sp. and whose genetic product is effective against the European corn borer and/or the western corn rootworm. Particularly preferred is a heterologous gene that originates from *Bacillus thuringiensis*.

Within the context of the present invention, the composition of the invention alone or in an appropriate formulation is applied to the seed. Preferably the seed is treated in a situation that is stable enough that no damage results from the treatment. In general seed may be treated at any time between harvest and sowing. Customarily seed is used that has been separated from the plant and extricated from the cob, pod, stem, husk, wool, or receptacle.

In general, care must be taken when treating the seed to select the amount of the composition of the invention that will be applied to the seed and/or other additives so that the germination of the seed is not compromised and the plant that emerges is not damaged. This should primarily be kept in mind for active ingredients that can have phytotoxic effects in certain application quantities.

The compositions of the invention can be applied directly, that is without containing other components or being diluted. As a rule is preferable to apply the composition in the form of a formulation suitable to the seed. Suitable formulations and processes for treating seed are known to persons skilled in the art and are described, e.g., in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The combinations of active ingredients can be transformed into the usual formulations, such as solutions, emulsions, wettable powders, suspensions, powders, dusts, pastes, soluble powders, granulates, suspension emulsion concentrates, natural and synthetic substances impregnated with the active ingredient and micro-encapsulations in polymer substances.

These formulations are produced in known manners, e.g., by mixing the active ingredients with extenders, i.e., solvents and/or solid carriers, if necessary using surfactants, i.e., emulsifiers and/or dispersants and/or foaming agents.

In the case of water being used as an extender, organic solvents, for example, can be used as auxiliary solvents. The primary liquid solvents include: aromatics, such as xylol, toluol and alkylnaphthalenes; chlorinated aromatics and chlorinated aliphatic hydrocarbons, such as chlorobenzenes, chloroethylenes, and methylene chloride; aliphatic hydrocarbons such as cyclohexane and paraffins, e.g., crude oil fractions, mineral and plant oils; alcohols, such as butanol or glycol, as well as their ethers and esters; ketones such as acetone, methyl ethyl ketone, methyl isobutyl ketone, and cyclohexane; highly polarized solvents, such as dimethyl formamide and dimethyl sulfoxide; and water.

Solid carriers include:
e.g., ammonium salts and natural crushed rock such as kaolins, aluminas, talc, chalk, silica, attapulgite, montmorillonite and diatomaceous earth, and synthetic crushed rock, such as highly disperse silicic acid, aluminium oxide and silicates; solid carriers for granulates include: e.g., crushed and fractionated natural stone such as calcite, marble, pumice, sepiolite, dolomite, as well as synthetic granulates made out of inorganic and organic rock flours, and granulates made out of organic material such as sawdust, coconut shells, corn cobs and tobacco stalks; emulsifiers and/or foaming agents include: e.g., non-ionogenic and anionic emulsifiers, such as polyoxyethylene fatty acid esters, polyoxyethylene fatty alcohol ethers, e.g., alkylaryl polyglycolether, alkylsulfonates, alkylsulfates, arylsulfonates as well as protein hydrolysates; dispersants include: e.g., lignosulfonate waste liquor and methyl cellulose.

In the formulations, deposit builders such as carboxymethylcellulose, natural and synthetic powdered, granulated or latex-shaped polymers may be used, such as gum arabic, polyvinyl alcohol, polyvinyl acetate, as well as natural phospholipids such as cephalines and lecithins and synthetic phospholipids. Additional additives may include mineral and vegetable oils.

Colorants such as inorganic pigments, e.g., iron oxide, titanium oxide, ferrocyanide blue and organic colorants, such as alizarin-, azo- and metalphthalocyanine dyes and trace nutrients such as salts of iron, manganese, boron, copper, cobalt, molybdenum and zinc can be used.

The formulations generally comprise between 0.1 and 95% w/w active ingredient, preferably between 0.5% and 90%.

The active ingredient combinations according to the invention can exist in customary formulations, as well as in the application forms prepared from these formulations in mixture with other active ingredients, such as insecticides, attractants, sterilants, bactericides, acaricides, nematicides, fungicides, growth-regulating agents and herbicides. Insecticides include, for example, phosphoric acid esters, carbamates, carbonic acid esters, chlorinated hydrocarbons, phenylurea, and substances produced by microorganisms.

The following are examples of particularly advantageous mixing partners:

Fungicides:
aldimorph, ampropylfos, ampropylfos-potassium, andoprim, anilazin, azaconazol, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulfide, capsimycin, captafol, captan, carbendazim, carboxin, carvone, chinomethionat, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazol, dichlofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadone, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoroimide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazol,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl; copper preparations, such as: copper hydroxide, copper naphthenate, copper oxychloride, copper sulfate, copper oxide, oxine copper and Bordeaux mixture,
mancopper, mancozeb, maneb, ferimzone, mepanipyrim, mepronil, metalaxyl, metconazole, methasulfocarb, methfuroxam, metiram, metomeclan, metsulfovax, mildiomycin, myclobutanil, myclozolin,
nickel-dimethyldithiocarbamate, nitrothal-isopropyl, nuarimol,
ofurace, oxadixyl, oxamocarb, oxolinic acid, oxycarboxin, oxythiinh,
paclobutrazol, pefurazoate, penconazole, pencycuron, phosdiphen, pimaricin, piperalin, polyoxin, polyoxorim, probenazole, prochloraz, procymidone, propamocarb, Propanosine-sodium, propiconazole, propineb, pyrazophos, pyrifenox, pyrimethanil, pyroquilon, pyroxyfur,
quinconazole, quintozene (PCMB),
sulfur and sulfur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazol, tridemorph, triflumizole, triforin, triticonazole, uniconazole,
validamycin A, vinclozolin, diniconazol,
zarilamid, zineb, ziram as well as
dagger G
OK-8705,
OK-8801,
α-(1,1-dimethylethyl)-β-(2-phenoxyethyl)-1H-1,2,4-triazole-1-ethanol,
α-(2,4-dichlorophenyl)-β-fluor-b-propyl-1H-1,2,4-triazole-1-ethanol,
α-(2,4-dichlorophenyl)-β-methoxy-α-methyl-1H-1,2,4-triazole-1-ethanol,
(5RS,6RS)-6-hydroxy-2,2,7,7-tetramethyl-5-(1H-1,2,4-triazole-1-yl)-3-octanone,
(E)-α-(methoxyimino)-N-methyl-2-phenoxy-phenylacetamide,
{2-methyl-1-[[[1-(4-methylphenyl)-ethyl]-amino]-carbonyl]-propyl}-carbamic acid-1-isopropylester
1-(2,4-dichlorophenyl)-2-(1H-1,2,4-triazole-1-yl)-ethanone-O-(phenylmethyl)-oxime,
1-(2-methyl-1-naphthalenyl)-1H-pyrrol-2,5-dion,
1-(3,5-dichlorophenyl)-3-(2-propenyl)-2,5-pyrrolidindione,
1-[(diiodomethyl)-sulfonyl]-4-methyl-benzol,
1-[[2-(2,4-dichlorophenyl)-1,3-dioxolane-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropane carboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethy)-sulfonyl]-5-(trichloromethyl)-1,3,4-thiadiazole,
2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile,
2-aminobutane,
2-bromo-2-(bromomethyl)-pentane dinitril,
2-chloro-N-(2,3-dihydro-1,1,3-trimethyl-1H-indene-4-yl)-3-pyridine carboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyan[(1-methyl-2-propynyl)-oxy]-methyl]-benzamide,
3-(1,1-dimethylpropyl-1-oxo)-1H-indene-2-carbonitrile,
3-[2-(4-chlorophenyl)-5-ethoxy-3-isoxazolidinyl]-pyridine, 4-chloro-2-cyan-N,N-dimethyl-5-(4-methylphenyl)-1H-imidazole-1-sulfonamide,
4-methyl-tetrazolo[1,5-a]quinazolin-5(4H)-one,
8-(1,1-dimethylethyl)-N-ethyl-N-propyl-1,4-dioxaspiro[4.5]decan-2-methanamine,
8-hydroxy quinoline sulfate,
9H-xanthene-9-carboxylic acid-2-[(phenylamino)-carbonyl]-hydrazide,
bis-(1-methylethyl)-3-methyl-4-[3-methylbenzoyl)-oxy]-2,5-thiophene dicarboxylate,
cis-1-(4-chlorophenyl)-2-(1H-1,2,4-triazole-1-yl)-cycloheptanol,
cis-4-[3-[4-(1,1-dimethylpropyl)-phenyl-2-methylpropyl]-2,6-dimethyl-morpholin-hydrochloride,
ethyl-[(4-chlorophenyl)-azo]-cyanoacetate,
potassium hydrogen carbonate,
methane tetrathiol sodium salt,
methyl-1-(2,3-dihydro-2,2-dimethyl-1H-indene-1-yl)-1H-imidazole-5-carboxylate,
methyl-N-(2,6-dimethylphenyl)-N-(5-isoxazolylcarbonyl)-DL-alaninate,
methyl-N-(chloroacetyl)-N-(2,6-dimethylphenyl)-DL-alaninate,
N-(2,3-dichloro-4-hydroxyphenyl)-1-methyl-cyclohexane carboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzene sulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropane carboxamide,
N-[2,2,2-trichloro-1-[(chloracetyl)-amino]-ethyl]-benzamide,
N-[3-chloro-4,5-bis-(2-propinyloxy)-phenyl]-N-methoxy-methanimidamide,
N-formyl-N-hydroxy-DL-alanine-sodium salt,
O,O-diethyl-[2-(dipropylamino)-2-oxoethyl]-ethylphosphoramidothioate,
O-methyl-S-phenyl-phenyl propyl phosphoramidothioate,
S-methyl-1,2,3-benzothiadiazole-7-carbothioate,
spiro[2H]-1-benzopyran-2,1'(3'H)-isobenzofuran]-3'-one.
Bactericides:
bronopol, dichlorophen, nitrapyrin, nickel dimethyldithiocarbamate, kasugamycin octhilinone, furan-carboxylic acid, oxytetracycline, probenazole, streptomycin, tecloftalam, copper sulfate and other copper formulations.
Insecticides/Acaricides/Nematicides
1. Acetylcholinesterase (AChE) Inhibitors
1.1 Carbamates, for Example
    alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb triazamate
1.2 Organophosphates, for Example
    acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-s-methyl, demeton-s-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion
2. Sodium Channel Modulators/Voltage Dependent Sodium Channel Blockers
2.1 Pyrethroids, for Example
    acrinathrin, allethrin (d-cis-trans, d-trans), beta-cyfluthrin, bifenthrin, bioallethrin, bioallethrin ((S)-cyclopentyl isomer), bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrethrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, teralethrin, tetramethrin (1R-isomer), tralomethrin, trans-fluthrin, ZXI 8901, pyrethrins (pyrethrum)
    DDT
2.2 Oxadiazines, for Example, Indoxacarb
3. Acetylcholine-Receptor Agonists/Antagonists
3.1 chloronicotiyinyls, for Example
    acetamiprid, clothianidin, dinotefuran, imidacloprid, nitenpyram, nithiazine, thiacloprid, thiamethoxam
3.2 Nicotine, Bensultap, Cartap
4. Acetylcholine-Receptor-Modulators
4.1 Spinosyns, for Example Spinosad
5. GABA-Regulated Chloride-Channel Antagonists
5.1 Cyclodiene Organochlorines, for Example
    camphechlor, chlordane, endosulfan, gamma-HCH, HCH, heptachlor, lindane, methoxychlor
5.2 Fiproles, for Example
    acetoprole, ethiprole, fipronil, vaniliprole
6. Chloride-Channel Activators
6.1 Mectins, for Example
    avermectin, emamectin, emamectin-benzoate, ivermectin, milbemycin
7. Juvenile-Hormone Mimics, for Example
    diofenolan, epofenonane, fenoxycarb, hydroprene, kinoprene, methoprene, pyriproxyfen, triprene
8. Ecdysone Agonists/Disruptors
8.1 diacylhydrazine, for Example
    chromafenozide, halofenozide, methoxyfenozide, tebufenozide 9. Chitin Biosynthesis Inhibitors
9.1 Benzoylureas, for Example
   bistrifluoron, chlorfluazuron, diflubenzuron, fluazuron, flucycloxuron, flufenoxuron, hexaflumuron, lufenuron, novaluron, noviflumuron, penfluoron, teflubenzuron, triflumuron
9.2 Buprofezin
9.3 Cyromazine
10. Oxidative Phosphorylation Inhibitors, ATP Disruptors
10.1 Diafenthiuron
10.2 Organotins, for Example Azocyclotin, Cyhexatin, Fenbutatin-Oxide
11. Uncouping Oxidative Phosphorylation by Short Circuiting the H Proton Gradient
11.1 Pyrroles, for Example Chlorfenapyr
11.2 Dinitrophenols, for Example Binapacryl, Dinobuton, Dinocap, DNOC
12. Site-I Electron Transport Inhibitors
12.1 METI's, for Example Fenazaquin, Fenpyroximate, Pyrimidifen, Pyridaben, Tebufenpyrad, Tolfenpyrad
12.2 Hydramethylnon
12.3 Dicofol
13. Site-II Electron Transport Inhibitors
   rotenone
14. Site-III Electron Transport Inhibitors
   acequinocyl, fluacrypyrim
15. Microbial Disruptors of Insect Mid-Gut Membranes
   *Bacillus thuringiensis* strains
16. Fat-Synthesis Inhibitors
   tetronic acids, for example
      spirodiclofen, spiromesifen
   tetramic acids, for example
      3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-reg.-no.: 382608-10-8) and carbonic acid, cis-3-(2,5-dimethylphenyl)-8-methoxy-2-oxo-1-azaspiro[4.5]dec-3-ene-4-yl ethyl ester (CAS-reg.-no.: 203313-25-1)
17. Carboxamides, for Example Flonicamid
18. Octopaminergic Agonists, for Example Amitraz
19. Magnesium-Stimulated ATPase Inhibitors, for Example Propargite
20. BDCAs, for Example N2-[1,1-dimethyl-2-(methyl sulfonyl)ethyl]-3-iodo-N1-[2-methyl-4-[1,2,2,2-tetrafluoro-1-(trifluoromethyl)ethyl]phenyl]-1,2-benzene dicarboxamide (CAS reg. no.: 272451-65-7)
21. Nereistoxin Analogues, for Example Thiocyclam Hydrogen Oxalate, Thiosultap Sodium
22. Biological Agents, Hormones or Pheromones, for Example
   azadirachtin, *bacillus* spp., *Beauveria* spp., codlemone, *metarrhizium* spp., *Paecilomyces* spp., Thuringiensin, *Verticillium* spp.
23. Active Ingredients with Unknown or Non-Specific Mechanisms of Action
23.1 Fumigants, for Example
   aluminium phosphide, methyl bromide, sulfuryl fluoride
23.2 Selective Antifeedants, for Example
   cryolite, flonicamid, pymetrozine
23.3 Mite Growth Inhibitors, for Example
   clofentezine, etoxazole, hexythiazox
23.4 amidoflumet, benclothiaz, benzoximate, bifenazate, bromopropylate, buprofezin, chinomethionat, chlordimeform, chlorobenzilate, chloropicrin, clothiazoben, cycloprene, dicyanil, fenoxacrim, fentrifanil, flubenzimine, flufenerim, flufenzin, gossyplure, hydramethylnone, japonilure, metoxadiazone, petroleum, piperonyl butoxide, potassium oleate, pyridalyl, sulfluramid, tetradifon, tetrasul, triarathene, verbutin, and (1R-cis)-[5-(phenylmethyl)-3-furanyl]-methyl-3-[(dihydro-2-oxo-3(2H)-furanylidend)-methyl]-2,2-dimethyl cyclopropane carboxylate (3-phenoxyphenyl)-methyl-2,2,3,3-tetramethyl cyclopropane carboxylate 1-[(2-chloro-5-thiazolyl)methyl]tetrahydro-3,5-dimethyl-N-nitro-1,3,5-triazine-2(1H)-imine 2-(2-chlor-6-fluorphenyl)-4-[4-(1,1-dimethylethyl)phenyl]-4,5-dihydro-oxazole 2-(acetyloxy)-3-dodecyl-1,4-naphthalendione 2-chloro-N-[[[4-(1-phenylethoxy)-phenyl]-amino]-carbonyl]-benzamide 2-chloro-N-[[[4-(2,2-dichloro-1,1-difluorethoxy)-phenyl]-amino]-carbonyl]-benzamide 3-methylphenyl-propyl carbamate 4-[4-(4-ethoxyphenyl)-4-methylpentyl]-1-fluoro-2-phenoxy-benzole 4-chloro-2-(1,1-dimethylethyl)-5-[[2-(2,6-dimethyl-4-phenoxyphenoxy)ethyl]thio]-3(2H)-pyridazinone 4-chloro-2-(2-chloro-2-methylpropyl)-5-[(6-iodo-3-pyridinyl)methoxy]-3(2H)-pyridazinone 4-chloro-5-[(6-chloro-3-pyridinyl)methoxy]-2-(3,4-dichlorphenyl)-3(2H)-pyridazinone

*Bacillus thuringiensis* strain EG-2348 benzoic acid [2-benzoyl-1-(1,1-dimethylethyl)-hydrazide butyric acid 2,2-dimethyl-3-(2,4-dichlorophenyl)-2-oxo-1-oxaspiro[4.5]dec-3-ene-4-yl-ester

[3-[(6-chloro-3-pyridinyl)methyl]-2-thiazolidinylidene]-cyanamide dihydro-2-(nitromethylene)-2H-1,3-thiazine-3(4H)-carboxaldehyde ethyl-[2-[[1,6-dihydro-6-oxo-1-(phenylmethyl)-4-pyridazinyl]oxy]ethyl]-carbamate N-(3,4,4-trifluor-1-oxo-3-butenyl)-glycine N-(4-chlorophenyl)-3-[4-(difluoromethoxy)phenyl]-4,5-dihydro-4-phenyl-1H-pyrazole-1-carboxamide N-methyl-N'-(1-methyl-2-propenyl)-1,2-hydrazine dicarbothioamide N-methyl-N'-2-propenyl-1,2-hydrazine dicarbothioamide O,O-diethyl-[2-(dipropylamino)-2-oxoethyl]-ethyl phosphoroamidothioate A mixture with other known active ingredients, such as herbicides or fertilizers or growth regulators is also possible.

The active ingredient combinations according to the invention can furthermore be used as insecticides in their customary formulations, as well as in the application forms prepared from these formulations in a mixture with synergistic agents. Synergistic agents are compounds through which the effect of the active ingredients is enhanced, while the applied synergistic agent itself does not need to be actively effective.

The content of the active ingredient of the application forms prepared from the customary formulations can vary widely. The active ingredient concentration of the application forms can range from 0.0000001 to 95% w/w of the active ingredient, preferably between 0.0001 and 1% w/w.

The active ingredients are applied in a customary manner appropriate for the application forms.

For application to sanitation-related and stored product pests, the active ingredient combinations distinguish themselves with an outstanding residual effect on wood and clay, as well as with good alkali stability on limed substrates.

The active ingredient combinations according to the invention act not only against plant, sanitation and stored-product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order Anoplura, e.g., *Pediculus humanus corporis, Haematopinus* spp., *Linognathus* spp., *Trichodectes* spp., *Damalinia* spp.

From the order *Mallophaga* and the subclasses Amblycera and Ischnocera e.g., *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the subclasses Nematocera and Brachycera e.g., *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order Siphonaptera e.g., *Pulex* spp., *Ctenocephalides* spp., *Xenopsylla* spp., *Ceratophyllus* spp.

From the order Heteroptera e.g., *Cimex* spp., *Triatoma* spp., *Rhodnius* spp., *Panstrongylus* spp.

From the order Blattaria, e.g., *Blatta orientalis, Periplaneta americana, Blattella germanica, Supella* spp.

From the subclass Acari (Acarina) and the orders Meta- and Mesostigmata e.g., *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order Actineda (Prostigata) and Acarida (Astigmata) e.g., *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active ingredient combinations according to the invention are also suitable for controlling arthropods that afflict agricultural livestock, such as cattle, sheep, goats, horses, hogs, donkeys, camels, buffalo, rabbits, chickens, turkeys, ducks, geese and bees; other pets, such as dogs, cats, caged birds and aquarium fish, and also so-called test animals, such as hamsters, guinea pigs, rats and mice. By controlling these arthropods, cases of death and reduction in productivity (of meat, milk, wool, hides, eggs, honey, etc.) should be decreased, so that more economic and easier animal husbandry is possible by use of the active ingredient combinations according to the invention.

The active ingredient combinations according to the invention are used in the veterinary sector in the customary manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear tags, tail tags, limb bands, halters, marking devices and the like.

When used for cattle, poultry, pets and the like, the active ingredient can be used as formulations (for example powders, emulsions, free-flowing agents), which contain the active ingredients in an amount of 1 to 80% w/w, directly or after 100- to 10.000-fold dilution, or they can be used as a chemical bath.

It has furthermore been found that the active ingredient combinations according to the invention have a strong insecticidal action against insects that destroy industrial materials.

The following insects are listed as examples and as being preferred—but without being limited to such:

Beetles such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenoptera such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Silverfish such as *Lepisma saccharina*.

Industrial materials in the present context are to be understood as meaning non-living materials, such as, preferably, plastics, adhesives, glues, papers and cardboard, leather, wood and processed wood products and coating materials.

Wood and processed wood products are especially preferred materials to be protected from insect infestation.

Wood and processed wood products that can be protected by the agent according to the invention or mixtures comprising such are to be understood to be, for example:

building timber, wooden beams, railway ties, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active ingredient combinations can be used as such, in the form of concentrates or in generally customary formulations, such as powders, granulates, solutions, suspensions, emulsions or pastes.

The formulations mentioned can be prepared in a known manner per se, for example by mixing the active ingredients with at least one solvent or diluent, emulsifier, dispersing agent and/or binder or fixing agent, a water repellent, if appropriate, siccatives and UV stabilizers and, if appropriate, dyes and pigments, and also other processing auxiliary agents.

The insecticidal agents or concentrates used for the preservation of wood and wood-derived timber products comprise the active ingredient according to the invention in a concentration of 0.0001 to 95% w/w, in particular 0.001 to 60% w/w.

The amount of the compositions or concentrates used depends on the nature and occurrence of the insects and on the medium. The optimum amount employed can be determined by a series of tests for each application. In general, however, it is sufficient to use 0.0001 to 20% w/w, preferably 0.001 to 10% w/w, of the active ingredient, based on the material to be preserved.

Solvents and/or diluents can be organic chemical solvents or solvent mixtures and/or oily or oil-like organic chemical solvents or solvent mixtures of low volatility and/or polar organic chemical solvents or solvent mixtures and/or water, and, if appropriate, an emulsifier and/or wetting agent.

Organic chemical solvents which are preferably used are oily or oil-like solvents having an evaporation rate over 35 and a flashpoint over 30° C., preferably over 45° C. Such oily or oil-like water-insoluble solvents of low volatility can be appropriate mineral oils or aromatic fractions thereof, or solvent mixtures containing mineral oils, preferably solvent naphtha, petroleum and/or alkyl benzene.

Mineral oils having a boiling range from 170 to 220° C., solvent naphtha having a boiling range from 170 to 220° C., spindle oil having a boiling range from 250 to 350° C., petroleum or aromatics having a boiling range from 160 to 280° C., turpentine oil and the like, are advantageously used.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility that have a relative evaporation rate over 35 and a flashpoint over 30° C., preferably over 45° C., can be replaced in part by organic chemical solvents of high or medium volatility, providing that the solvent mixture likewise has a relative evaporation rate of over 35 and a flashpoint over 30° C., preferably over 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as glycol ethers, esters and the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example, polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be used in the form of an emulsion, dispersion or solution. Bitumen or bituminous substances can also be used as binders in an amount of up to 10% w/w. Dyestuffs, pigments, water-repelling agents, odour correctants and inhibitors or anticorrosive agents and the like which are known per se can additionally be used.

It is preferred according to the invention for the composition or concentrate to contain, as the organic chemical binder, at least one alkyd resin or modified alkyd resin and/or one drying vegetable oil. Alkyd resins having an oil content of more than 45% w/w, preferably 50 to 68% w/w, are preferably used according to the invention.

All or some of the binder mentioned can be replaced by a fixing agent (mixture) or a softener (mixture). These additives are intended to prevent evaporation of the active ingredients and crystallization or precipitation. They preferably replace 0.01 to 30% of the binder (based on 100% of the binder used).

The softeners originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluene sulfonic acid esters.

Fixing agents are based chemically on polyvinyl alkyl ethers, such as polyvinyl methyl ether or ketones, such as benzophenone or ethylene benzophenone.

Water, in particular, can be considered as a solvent or diluent, if appropriate, mixed with one or more of the above-mentioned organic chemical solvents or diluents, emulsifiers or dispersing agents.

Particularly effective wood preservation is achieved by impregnation processes done on a large industrial scale, for example, vacuum, double vacuum or pressure processes.

The ready-to-use compositions can also comprise other insecticides, if appropriate, and also one or more fungicides, if appropriate.

The active ingredient combinations according to the invention can at the same time be used for protecting objects which come into contact with salt water or brackish water, such as hulls, screens, nets, structures, moorings and signalling systems, against fouling.

Fouling by sessile Oligochaeta, such as fan worms, and by molluscs and species from the Lepadomorpha suborder (goose barnacles), such as various Lepas and Scalpellum species, or by species from the Balanomorpha suborder (acorn barnacles), such as *Balanus* or *Pollicipes* species, increases the frictional drag of ships and, as a consequence, results in a marked increase in operational costs owing to higher energy consumption and, furthermore, frequent time in dry dock.

Apart from fouling by algae, for example *Ectocarpus* sp. and *Ceramium* sp., fouling by sessile Entomostraca groups, which are grouped under Cirripedia (cirriped crustaceans), is of particular importance.

Surprisingly, it has now been found that the active ingredient combinations according to the invention have an outstanding antifouling effect.

Using the active ingredient combinations according to the invention allows the use of heavy metals such as in bis-(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylene bisthiocarbamate, zinc dimethyl dithiocarbamate, zinc ethylene bisthiocarbamate, zinc salts and copper salts of 2-pyridinethiol 1-oxide, bisdimethyl dithiocarbamoyl zinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling coatings can additionally comprise other active ingredients, preferably algaecides, fungicides, herbicides, molluscicides, or other antifouling active ingredients.

Preferably suitable combination partners with the antifouling agents according to the invention are:

Algaecides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as
azaconazole, cyproconazole, epoxyconazole, hexaconazole, metconazole, propiconazole and tebuconazole;

molloscicides such as
iron chelating agents, fentin acetate, metaldehyde, methiocarb, niclosamid, thiodicarb and trimethacrb;

or conventional antifouling active ingredients such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(-methylsulphonyl)-pyridine, 2,4,5,6-tetrachloroisophthalonitrile, tetramethylthiuram disulphide and 2,4,6-trichlorophenylmaleimide.

The antifouling compositions used comprise the active ingredient in a concentration of 0.001 to 50% w/w, in particular 0.01 to 20% by weight.

Moreover, the antifouling compositions comprise the customary components such as those described in Ungerer, Chem. Ind. 1985, 37, 730-732 and Williams, Antifouling Marine Coatings, Noyes, Park Ridge, 1973.

Besides the algaecidal, fungicidal, molluscicidal and insecticidal active ingredients, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise softeners, modifiers which affect the rheological properties and other conventional components. The active ingredient combinations according to the invention may also be incorporated into self-polishing antifouling systems.

The active ingredient combinations according to the invention are also suitable for controlling animal pests, in particular insects, arachnids and mites, that are found in enclosed spaces such as dwellings, factory floors, offices, vehicle passenger cabins and the like. They can be used alone in household insecticide products for controlling these pests or in combination with other active ingredients and auxiliaries. They are effective for sensitive and resistant species as well as for all life stages. These pests include:

From the order Scorpionidae, e.g., *Buthus occitanus*.

From the order Acaria, e.g., *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order Araneae, e.g., Aviculariidae, Araneidae.

From the order Opiliones, e.g., *Pseudoscorpiones chelifer, Pseudoscorpiones cheiridium, Opiliones phalangium*.

From the order Isopoda, e.g., *Oniscus asellus, Porcellio scaber*.

From the order Diplopoda, e.g., *Blaniulus guttulatus, Polydesmus* spp.

From the order Chilopoda, e.g., *Geophilus* spp.

From the order Zygentoma, e.g., *Ctenolepisma* spp., *Lepisma saccharina, Lepismodes inquilinus*.

From the order Blattaria, e.g., *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order Saltatoria, e.g., *Acheta domesticus*.

From the order Dermaptera, e.g., *Forficula auricularia*.

From the order Isoptera, e.g., *Kalotermes* spp., *Reticulitermes* spp.

From the order Psocoptera, e.g., *Lepinatus* spp., *Liposcelis* spp.

From the order Coleptera, e.g., *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order Diptera, e.g., *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order Lepidoptera, e.g., *Achroia grisella, Galleria mellonella, Plodia interpunctella, Tinea cloacella, Tinea pellionella, Tineola bisselliella*.

From the order Siphonaptera, e.g., *Ctenocephalides canis, Ctenocephalides felis, Pulex irritans, Tunga penetrans, Xenopsylla cheopis*.

From the order Hymenoptera, e.g., *Camponotus herculeanus, Lasius fuliginosus, Lasius niger, Lasius umbratus, Monomorium pharaonis, Paravespula* spp., *Tetramorium caespitum*.

From the order Anoplura, e.g., *Pediculus humanus capitis, Pediculus humanus corporis, Phthirus pubis*.

From the order Heteroptera, e.g., *Cimex hemipterus, Cimex lectularius, Rhodinus prolixus, Triatoma infestans*.

They are used in the household insecticides sector alone or in combination with other suitable active ingredients such as phosphoric acid esters, carbamates, pyrethroids, growth regulators and active ingredients from other known classes of insecticides.

They are applied in aerosols, un-pressurised spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

When using the active ingredient combinations according to the invention the amounts being applied can be varied within a wide range depending on how they are being applied. When treating plant parts the application amount of active ingredient combinations being applied is in general between 0.1 and 10,000 g/ha, preferable between 10 and 1,000 g/ha.

The good insecticidal effect of the active ingredient combinations according to the invention is shown in the following examples. While the individual active ingredients have limitations regarding their effect, the combinations that exceeds the sum of the individual effects.

The expected effect for a given combination of two active ingredients can be calculated (cf. Colby, S. R., "Calculating Synergistic and Antagonistic Responses of Herbicide Combinations", Weeds, 15, pp. 20-22, 1967).

If

X=the kill rate, expressed in % of the untreated control, while using active ingredient A in an application amount of m ppm, Y=the kill rate, expressed in % of the untreated control, while using active ingredient B in an application amount of n ppm, E=the kill rate, expressed in % of the untreated control, while using active ingredient A and B in application amounts of m and n ppm, $$E = X + Y - \frac{X \times Y}{100}$$

then

If the actual kill rate is higher than calculated rate, the combination's kill rate is superadditive, i.e., it has a synergistic effect. In this case, the actually observed kill rate must be higher than the value calculated using the above formula for the expected kill rate (E).

EXAMPLE A

*Myzus persicae* Test

Solvent: 7 parts per weight dimethyl formamide
Emulsifiers: 2 parts by weight alkylaryl polyglycol ether To prepare one of the appropriate active ingredient preparations, mix 1 part by weight of the active ingredient with the indicated amount of solvent and emulsifier and dilute the concentrate with emulsifier-containing water to the desired concentration.

Cabbage leaves (*Brassica oleracea*) that have been highly infested with the green peach aphid (*Myzus persicae*) are treated by being dipped into the active ingredient preparation at the desired concentration.

After the desired time, determine the % that have been killed off. For these purposes, 100% means that all the aphids on the leaves were killed; 0% means that no aphids were killed. Calculate the determined kill values using Colby's formula.

In this test, the following combinations of active ingredients demonstrated, in accordance with the above statement, a synergistically improved efficacy in comparison to applying the active ingredients separately:

TABLE A

| | Plant-damaging Insects *Myzus persicae* Test | | |
|---|---|---|---|
| Active Ingredients | Concentration in ppm | Kill rate in % after $6^d$ | |
| | | det.* | calc.** |
| thiodicarb | 20 | 0 | |
| thiamethoxam | 0.8 | 85 | |
| thiodicarb + thiamethoxam (25:1) in accordance with the invention | 20 + 0.8 | 95 | 85 |

TABLE A-continued

| | Plant-damaging Insects *Myzus persicae* Test | | |
|---|---|---|---|
| Active Ingredients | Concentration in ppm | Dead in % after $6^d$ | |
| | | det.* | calc.** |
| thiodicarb | 20 | 0 | |
| thiacloprid | 0.8 | 30 | |
| thiodicarb + thiacloprid (25:1) in accordance with the invention | 20 + 0.8 | 50 | 30 |

*det. = determined effect
**calc. = effect calculated using Colby's formula

EXAMPLE B

*Phaedon cochleariae* Larvae Test

Solvent: 7 parts per weight dimethyl formamide
Emulsifiers: 2 parts by weight alkylaryl polyglycol ether To manufacture one of the appropriate active ingredient preparations, mix 1 part by weight of the active ingredient with the indicated amount of solvent and emulsifier and dilute the concentrate with emulsifier-containing water to the desired concentration.

Cabbage leaves (*Brassica oleracea*) are treated by being dipped into the active ingredient preparation at the desired concentration and infested with larvae of the mustard beetle (*Phaedon cochleariae*) while the leaves are still damp.

After the desired time, determine the % that have been killed off. For this purpose 100% means that all the beetle larvae on the leaves were killed; 0% means that no beetle larvae were killed. Calculate the determined kill values using Colby's formula.

In this test, the following combinations of active ingredients demonstrated, in accordance with the above statement, a synergistically improved efficacy in comparison to applying the active ingredients separately:

TABLE B

| | Plant-damaging Insects *Phaedon cochleariae* Larvae Test | | |
|---|---|---|---|
| Active Ingredients | Concentration in ppm | Kill rate in % after $6^d$ | |
| | | det.* | calc.** |
| thiodicarb | 100 | 15 | |
| clothianidin | 4 | 75 | |
| thiodicarb + clothianidin (25:1) in accordance with the invention | 100 + 4 | 100 | 79.75 |
| thiodicarb | 100 | 45 | |
| imidacloprid | 4 | 45 | |
| thiodicarb + imidacloprid (25:1) in accordance with the invention | 100 + 4 | 80 | 69.75 |
| thiodicarb | 100 | 15 | |
| thiacloprid | 4 | 0 | |
| in accordance with the invention thiodicarb + thiacloprid (25:1) | 100 + 4 | 65 | 15 |

TABLE B-continued

Plant-damaging Insects
*Phaedon cochleariae* Larvae Test

| Active Ingredients | Concentration in ppm | Kill rate in % after 6$^d$ | |
|---|---|---|---|
| | | det.* | calc.** |
| thiodicarb | 100 | 45 | |
| thiamethoxam | 4 | 25 | |
| in accordance with the invention thiodicarb + thiamethoxam (25:1) | 100 + 4 | 85 | 58.75 |

*det. = determined effect
**calc. = effect calculated using Colby's formula

EXAMPLE C

*Plutella-xylostella* Test (Resistant Strain)
Solvent: 7 parts per weight dimethyl formamide
Emulsifier: 2 parts by weight alkylaryl polyglycol ether To prepare one of the appropriate active ingredient preparations, mix 1 part by weight of the active ingredient with the indicated amount of solvent and emulsifier and dilute the concentrate with emulsifier-containing water to the desired concentration.

Cabbage leaves (*Brassica oleracea*) are treated by being dipped into the active ingredient preparation at the desired concentration and infested with diamondback moth grubs (*Plutella xylostella*, resistant strain) while the leaves are still damp.

After the desired time, determine the % that have been killed off. For these purposes 100% means that all the grubs on the leaves were killed; 0% means that no grubs were killed. Calculate the determined kill rate values using Colby's formula.

In this test, the following combinations of active ingredients demonstrated, in accordance with the above statement, a synergistically improved efficacy in comparison to applying the active ingredients separately:

TABLE D

Plant-damaging Insects
*Plutella xylostella* (resistant strain) Test

| Active Ingredients | Concentration in ppm | Kill rate in % after 6$^d$ | |
|---|---|---|---|
| | | det.* | calc.** |
| thiodicarb | 100 | 15 | |
| thiacloprid | 100 | 45 | |
| thiodicarb + thiacloprid (1:1) in accordance with the invention | 100 + 100 | 90 | 53.25 |
| thiodicarb | 100 | 5 | |
| thiamethoxam | 100 | 75 | |
| thiodicarb + thiamethoxam (1:1) in accordance with the invention | 100 + 100 | 95 | 76.25 |

*det. = determined effect
**calc. = effect calculated using Colby's formula

The invention claimed is:

1. A composition comprising a synergistically effective mixture of thiodicarb and clothianidin, and optionally extenders and/or surfactants, wherein the weight ratio of thiodicarb to clothianidin is between 25:1 and 1:5.

2. A method of controlling animal pests comprising applying the composition of claim 1 to the area to be rid of said pests.

3. A composition comprising a synergistically effective mixture of thiodicarb and clothianidin as the only active ingredients, and optionally extenders and/or surfactants, wherein the weight ratio of thiodicarb to clothianidin is between 25:1 to 1:5.

4. A method of controlling animal pests comprising applying the composition of claim 3 to the area to be rid of said pests.

* * * * *